United States Patent [19]

Yamawaki et al.

[11] 4,430,229

[45] Feb. 7, 1984

[54] IMMUNE ADSORBENT AND ADSORBING DEVICE

[75] Inventors: Naokuni Yamawaki; Katsunori Horikoshi, both of Fuji, Japan

[73] Assignee: Asahi Kasei Kogyo Kabushiki Kaisha, Osaka, Japan

[21] Appl. No.: 378,924

[22] Filed: May 17, 1982

[30] Foreign Application Priority Data

May 22, 1981 [JP] Japan .................................. 56-76776
Dec. 3, 1981 [JP] Japan ................................. 56-193735

[51] Int. Cl.³ .............................................. B01D 15/00
[52] U.S. Cl. .................................... 210/692; 210/263;
210/927; 210/502.1; 502/150
[58] Field of Search ........................ 210/660, 690–692,
210/502, 506, 908, 927, 263, 287; 252/426, 430

[56] References Cited

U.S. PATENT DOCUMENTS 3,972,818 8/1976 Bokros .................................. 210/927
4,061,591 12/1977 Oliver et al. ......................... 252/430

FOREIGN PATENT DOCUMENTS 55-36277 3/1980 Japan .

Primary Examiner—Ivars C. Cintins
Attorney, Agent, or Firm—Sprung, Horn, Kramer & Woods

[57] ABSTRACT

An immune adsorbent for autoantibodies and/or immune complexes is provided which is comprised of a water-insoluble carrier and at least one low-molecular-weight substance containing a purine base or pyrimidine base as a constituent element, which is fixed to said carrier. The immune adsorbent is usually used in an adsorption apparatus comprising a vessel having fluid inlet and outlet openings and having packed therein said immune adsorbent.

9 Claims, 2 Drawing Figures

IMMUNE ADSORBENT AND ADSORBING DEVICE

BACKGROUND OF THE INVENTION (1) Field of the Invention

This invention relates to an immune adsorbent for use in removing autoantibodies, such as anti-DNA antibodies, anti-ENA antibodies and antinuclear antibodies and/or immune complexes from blood, plasma and other body fluids, and also to an adsorption apparatus comprising this adsorbent. The adsorbent and adsorption apparatus of the present invention are especially effective for selectively adsorbing and removing autoantibodies and/or immune complexes present in body fluids of patient's suffering from collagen diseases represented by systemic lupus erythematodes (hereinafter referred to as "SLE", for brevity), thereby purifying the body fluids, which leads to arrest of the spread of said diseases, relief to the patients suffering from said diseases and expedites curing of the diseases.

(2) Description of the Prior Art

SLE is an intractable disease which is often observed in young adults, especially young women, and which affects general organs, especially vascular tissues and connective tissues, and it is a typical example of an autoimmune disease. The cause of SLE has been unknown, but it now is considered that the presence of antinuclear antibodies and other autoantibodies in the blood of a patient suffering from SLE has serious influences on the occurrence of various disorders. Furthermore, the mechanism of depositing antigen-antibody immune complexes onto tissues is considered to have an important relation to the occurrence of vasculitis and nephritis. Recently, the plasma exchange treatment for removing malignant substances, such as antigens, antibodies and immune complexes found in the plasma of a patient, was accomplished by exchanging the patient's plasma with fresh frozen plasma or an albumin preparation, and it is confirmed that considerable effects of arresting the spread of diseases, relieving the suffering of patients and curing the diseases can be attained by this treatment.

However, this plasma exchange treatment is defective in that (1) it is difficult to readily procure a large amount of fresh frozen plasma or plasma components to replace the patient's plasma and (2) since another's plasma is utilized, the risk of infection with the hepatitis virus is very high.

As another means for removing malignant substances from the plasma of a patient, there is known an ultrafiltration method using an ultrafilter membrane. Although this method is advantageous in that the amount of plasma components supplied can be reduced, this method is defective in that (1) malignant substances having a molecular weight within a certain range are not always completely removed, (2) since the removal capacity depends solely on the molecular weight, some valuable substances are inevitably removed, and (3) if the membrane becomes clogged, such troubles as reduction of the filtration speed and change of the cut-off molecular weight occur.

Furthermore, there has been proposed a method in which autoantibodies are removed by utilizing an antigen-antibody reaction wherein an adsorbent comprising a natural polymer or similar polymers, such as DNA or a synthetic nucleic acid polymer is used, which polymer is fixed on a carrier. However, this method is poor in practical use because (i) the substance to be fixed on the carrier is expensive and (ii) if the fixed substance, which is an antigen, is set free during the treatment and introduced in the body fluid of a patient, it is liable to cause another disease.

SUMMARY OF THE INVENTION

It is, therefore, a primary object of the present invention to provide an immune adsorbent characterized in that (i) the capacity of selectively removing malignant substances, such as autoantibodies and immune complexes, from the plasma of a patient is very high, (ii) even if the absorbing ingredient becomes separated from the carrier and introduced in the body fluid of the patient, it does no harm to the body of the patient and (iii) it can be handled very easily.

Another object of the present invention is to provide an adsorption apparatus comprising the above-mentioned absorbent.

In accordance with one fundamental aspect of the present invention, there is provided an adsorbing material for autoantibodies and/or immune complexes comprising a water-insoluble carrier and at least one member selected from low-molecular-weight substances containing a purine base or pyrimidine base as a constituent element, which is fixed to said carrier.

In accordance with another fundamental aspect of the present invention, there is provided an apparatus for the adsorption of autoantibodies and/or immune complexes, which comprises a vessel having fluid inlet and fluid outlet openings and at least one adsorbing material packed in said vessel, said adsorbing material comprising a water-insoluble carrier and at least one member selected from low-molecular-weight substances containing a purine base or pyrimidine base as a constituent element, which is fixed to said carrier.

DESCRIPTION OF THE PREFERRED EMBODIMENT

Figure 1:
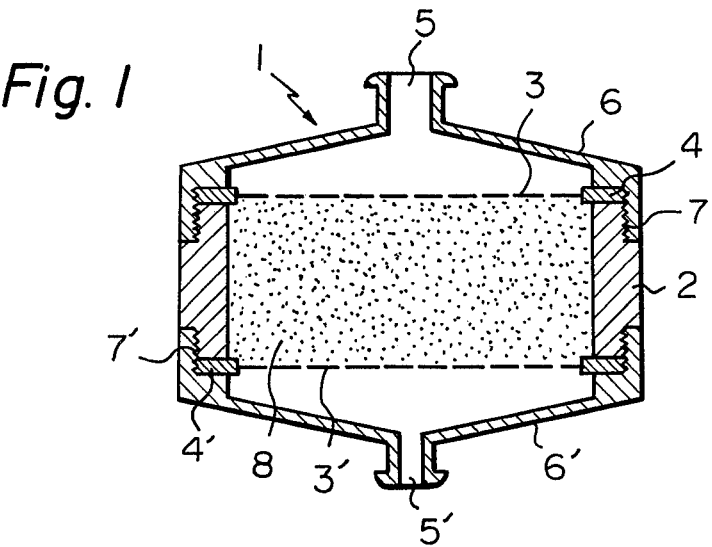
FIG. 1 is a sectional view illustrating one embodiment of the adsorption apparatus according to the present invention.

The low-molecular-weight substance used in the present invention is a substance containing a purine base or pyrimidine base as a constituent element, which has a molecular weight lower than 10,000, preferably lower than 1,000. This low-molecular-weight substance is advantageous over a natural polymer, such as protein A (molecular weight=42,000), because it can be handled more easily at the fixing step and can be stored more easily and stably after the fixing treatment, and the sterilization operation can be performed very easily. Furthermore, even in the case where such a low-molecular-weight substance having a molecular weight lower than 10,000 is dissolved out from the carrier, the antigenicity of the substance to the living body is negligibly small.

As examples of the low-molecular-weight substance, there can be mentioned bases, such as adenine, cytosine, guanine, uracil, thymine, hypoxanthine and xanthine; nucleosides, such as adenosine, cytidine, guanosine, uridine, inosine, xanthosine, deoxyadenosine, deoxycytidine, deoxyguanosine, deoxyuridine and thymidine; nucleotides, such as adenosine 5'-phosphate, cytidine 5'-phosphate, guanosine 5'-phosphate, inosine 5'-phosphate, uridine 5'-phosphate; corresponding deoxyriboses, corresponding diphosphates and triphosphates and products formed by attaching phosphoric acid to 2'- or 3'-positions of the foregoing nucleotides; nucleotides to which saccharides, such as glucose and mannose, are bonded; oligonucleotides having a nucletide number smaller than 10; nucleotide coenzymes, such as nicotinamide-adenine dinucleotide (NAD), flavine-adenine dinucleotide (FAD), coenzyme A and coenzyme $B_{12}$; and derivatives of these compounds. Among the foregoing compounds, bases, nucleosides and nucleotides are preferred. Bases, particularly purine bases, such as adenine and guanine, are especially preferred. These compounds may be fixed to the carrier singly or in the form of a mixture of two or more.

Any of the water-insoluble carriers may be used in the present invention. However, in order to reduce non-specific adsorption, it is preferred that a hydrophilic carrier be used. The shape of the water-insoluble carrier is not particularly critical. Namely, the water-insoluble carrier may be in the form of a particle, fiber, hollow fiber or membrane. From the viewpoints of ease in handling, the ligand retention quantity and the effective area for contact with plasma, it is preferred that a particulate or fibrous carrier be used.

As the fibrous carrier, it is preferred that the fineness be 0.02 to 10 denier, especially 0.1 to 5 denier. If it is not so fine, the autoantibody adsorption quantity and speed are reduced. In contrast, if it is too fine, activation of the coagulation system, adhesion of blood cells and clogging readily occur. As fibers for the fibrous carrier, there are preferably used known hydrophilic fibers, such as regenerated cellulose fibers, nylon fibers, acrylic fibers and polyester fibers.

As the particulate carrier, it is preferred that the average particle size be in the range of from 25 to 2,500 $\mu$m, especially 150 to 1,500 $\mu$m. The average particle size is determined by classifying the particles in running water by using sieves specified in JIS Z-8801, determining the intermediate values in the respective fractions from upper limit and lower limit particle sizes in the respective fractions and calculating a weight average value from these intermediate values. The spherical shape is preferred, though the shape of the particles is not particularly critical. If the average particle size exceeds 2,500 $\mu$m, the malignant substance adsorption capacity and speed are reduced. In contrast, if the average particle size is smaller than 25 $\mu$m, in the case of extracorporeal circulation, the pressure loss is extreme and clogging is readily caused. Moreover, if the average particle size is smaller than 25 $\mu$m, activation of the coagulation system and adhesion of blood cells occur. As the material for the particulate carrier, there can be mentioned, for example, agarose, crosslinked dextran, cellulose, crosslinked polyacrylamide, porous silica beads, active carbon and porous glass. Furthermore, carriers customarily used for the fixation of enzymes and affinity chromatography may be used in the present invention.

As the particulate carrier, there can also advantageously be used a carrier composed of porous synthetic polymer particles. These polymer particles can fix the above-mentioned low-molecular-weight substance on the surfaces thereof, and they have fine pores having an average pore size of 300 to 9,000 Å, preferably 1,000 to 6,000 Å. As the polymer constituting these particles, there can be mentioned polyamides, polyesters, polyurethanes and vinyl compound polymers, but a hydrophilic porous polymer of a vinyl compound is especially preferred.

If the average pore size is too small, the amount of autoantibodies adsorbed is small and, in contrast, if the average pore size is too large, the strength of the polymer particles is reduced and the surface area is decreased.

The average pore size may be measured by a mercury intrusion type porosimeter. More specifically, mercury is intruded under pressure into a porous substance, and the pore volume is determined from the amount of mercury intruded and the pore size is determined from the pressure required for intrusion. According to this method, pore sizes larger than 40 Å can be measured. The value of the pore size "r" when the value of dv/dlogr is maximum is defined as the average pore size. Incidentally, "v" in the above formula represents the accumulated pore volume.

Among the foregoing porous polymers, a hydroxyl group-containing crosslinked copolymer is especially preferred because (1) the mutual action between the copolymer and solutes in plasma, such as proteins, is small and non-specific adsorption can be controlled to a minimum level and (2) the mutual action between the copolymer and the complement or coagulation system is small. A carrier composed of a crosslinked copolymer comprising vinyl alcohol units as the main recurring units is especially excellent in the above-mentioned characteristics (1) and (2) and also is excellent in physical characteristics and heat resistance. Accordingly, heat sterilization of this carrier is possible. Moreover, this carrier retains excellent mechanical strength characteristics inherent to the synthetic polymer. Even when this carrier is used as the carrier for a whole blood adsorbent, it shows excellent properties. For example, the mutual action between the carrier and the hemocyte components is small, and occurrence of undesirable phenomena, such as thrombosis, non-specific adsorption of hemocyte components and residual blood, is substantially minimized.

As the density of hydroxyl groups in the crosslinked copolymer is increased, the hydrophilic characteristic is proportionally increased and the mutual action to the blood components is reduced, and, furthermore, if activation is effected by an activating agent, the active group density can be maintained at a high level. However, an increase of the hydroxyl group density results in a reduction of the mechanical strength and physical characteristics. In view of the foregoing, it is preferred that the hydroxyl group density be 5 to 17 meq/g, especially 6 to 15 meq/g.

The hydroxyl group density is determined according to the following procedures. More specifically, the carrier is reacted with acetic anhydride in pyridine as a solvent, and the amount of acetic anhydride consumed by the reaction with the hydroxyl groups or the increase in the weight of the carrier is measured. The hydroxyl group density is calculated from this amount of acetic anhydride consumed or the weight increase of the carrier. When 1 g of the dry carrier reacts with 1 millimol of acetic anhydride, the hydroxyl group density is 1 meq/g.

The hydroxyl group-containing crosslinked copolymers, inclusive of the crosslinked copolymer comprising vinyl alcohol units as the main recurring units, may be prepared according to various methods in which hydroxyl groups are introduced by (1) polymerization of a hydroxyl group-containing monomer, (2) chemical reaction of a polymer or (3) reaction with a hydroxyl group-containing crosslinking agent. These methods may be adopted in combination. A radical polymerization process may be adopted as the polymerization process. The crosslinking agent may be introduced at the polymerization step by means of copolymerization or by chemical reaction of the polymer (the reaction between polymers or the reaction of the polymer with the crosslinking agent). These crosslinking agent introducing methods may be adopted in combination.

For example, the intended crosslinked copolymer may be prepared by copolymerizing a vinyl monomer with a vinyl or allyl crosslinking agent and then hydrolyzing the resultant copolymer. As the vinyl monomer, there can be mentioned, for example, vinyl esters of carboxylic acids such as vinyl acetate and vinyl propionate; vinyl ethers such as methyl vinyl ether and ethyl vinyl ether; and vinylene carbonates. As the crosslinking agent, there can be mentioned, for example, allyl compounds such as triallyl isocyanurate and triallyl cyanurate; dimethacrylates and diacrylates such as ethylene glycol dimethacrylate and diethylene glycol dimethacrylate; polyvinyl ethers such as butanediol divinyl ether, diethylene glycol divinyl ether and tetravinyl glyoxazole; polyallyl ethers such as diallylidene pentaerythritol and tetraallyloxyethane; and glycidyl acrylate and glycidyl methacrylate. If desired, other comonomers may be copolymerized.

Of the vinyl copolymers, a triallyl isocyanurate-crosslinked polymer obtained by copolymerizing a vinyl ester of a carboxylic acid with a vinyl or allyl compound having an isocyanurate ring and then hydrolyzing the resultant copolymer is especially preferred because it gives a carrier excellent in strength, chemical stability and heat resistance.

Vinyl copolymers have been explained hereinbefore. However, it must be noted that the porous synthetic polymers that can be used in the present invention are not limited to the foregoing vinyl copolymers.

As pointed out hereinbefore, the hydroxyl group-containing polymer may be in the form of either a particle (inclusive of a spherical particle), a fiber, a hollow fiber or a flat membrane. However, in view of the surface area of the carrier (that is, the adsorbing capacity of the adsorbent) and the flowing of the body fluid upon extra-corporeal circulation, the porous particulate form is especially preferred. Accordingly, known suspension polymerization process are especially effective for the synthesis of the polymer carrier.

It is preferred that the specific surface area of the crosslinked copolymer be at least 5 m$^2$/g. The specific surface area referred to herein is one determined according to the most popular BET method using nitrogen. Namely, the specific surface area indicates the surface area occupied by adsorbed nitrogen gas per unit weight of the dry crosslinked copolymer. In other words, the specific surface area indicates how effectively the unit weight of the crosslinked polymer in the dry state forms the adsorbing surface. Incidentally, the sample to be used for determination of the specific surface area should be sufficiently dry. However, some of the crosslinked polymers that are used in the present invention are difficult to dry. In the case of these polymers, the sample carrier wetted with water is equilibrated with acetone, is dried under reduced pressure at a temperature lower than 60° C., and is then measured.

Ordinarily, a crosslinked copolymer is swollen in a medium having an affinity with the crosslinked copolymer and the copolymer is shrunk when dried. In the case of a soft gel in which pores filled with the medium at the time of swelling are supported only by a network structure, the network structure is destroyed on drying and the pores substantially disappear. In this case, the specific surface area is ordinarily very low and less than 1 m$^2$/g because only the periphery of the particles shows this value. Since agarose, heretofore used for affinity chromatography, is a soft gel, its pores disappear on drying. Accordingly, the sterilization of agarose cannot easily be accomplished. Furthermore, since agarose has a soft network structure which is readily destroyed, when it is used for extra-corporeal circulation, it is impossible to circulate the body fluid at a high flow rate for a long period of time.

The hydroxyl group-containing crosslinked copolymer advantageously used in the present invention is a hard gel wherein the pores are supported by a strong structure and which can sufficiently resist freeze-drying or heat sterilization. When the hard gel is dried, the pores contract to some extent, but the state of the pores at the time of swelling is substantially maintained. In short, the crosslinked copolymer has permanent pores and its specific surface area is larger than that of the soft gel and is ordinarily at least 5 m$^2$/g.

It is preferable that the amount of water retention (hereinafter referred to as "Wr" for brevity) of the crosslinked polymer used in the present invention be in the range of from 0.5 to 16 g/g, preferably from 1.0 to 15.0 g/g.

The Wr value is expressed by the amount of physiological saline solution contained in the particles of the crosslinked copolymer when the copolymer is equilibrated with physiological saline solution, per unit weight of the dry copolymer. In short, the Wr value is a parameter indicating the volume of pores in the crosslinked copolymer. As the Wr value is increased, the weight of the skeleton, namely, the crosslinked copolymer per se, per unit volume of the crosslinked copolymer in water is relatively reduced, with the result that the mechanical strength of the crosslinked copolymer in physiological saline solution, and thus in the body fluid, is reduced. When the Wr value is reduced, since the volume of pores effective for adsorption per unit weight or volume of the crosslinked copolymer is reduced, the adsorption capacity is reduced. Accordingly, it is preferred that the carrier used in the present invention have an appropriate Wr value.

The Wr value is determined according to the following procedures. At first, the weight ($W_2$) of the sufficiently dried crosslinked copolymer is measured and the copolymer is sufficiently equilibrated with physiological saline solution. Then the equilibrated crosslinked copolymer is subjected to centrifugal separation to remove the physiological saline solution adhering to the surface of the crosslinked copolymer, and the weight ($W_1$) of the residual copolymer is measured. The Wr value is calculated according to the following formula:

$$Wr\ (g/g) = \frac{W_1 - W_2}{W_2}$$

Since the molecular weights of the substance to be adsorbed is in the range of from about 150,000 (IgG) to about 10,000,000 (immune complex, especially IgM immune complex), it is preferred that the molecular weight exclusion limits ($M_{lim}$; for proteins) of the carrier be within the range of from 150,000 to about 10,000,000, and the molecular weight exclusion limits ($M_{lim}$) for attaining the objects of the present invention is in the range of from 1,000,000 to 5,000,000.

If only the above-mentioned low-molecular-weight substance is fixed to the carrier, the intended effect can be attained. The method for fixing the low-molecular-weight substance to the carrier is not particularly critical in the present invention. Ordinarily, there may be adopted any of the known methods such as the covalent bonding method, the ion bonding method, the physical adsorption method, the embedding method and the method of precipitation and insolubilization on the polymer surface. However, it is preferred that there be adopted the method in which the low-molecular-weight substance is fixed by the covalent bond and insolubilized because by this method the dissolution of the fixed substance is highly suppressed. In order to accomplish fixation by the covalent bond, the carrier may be activated according to a known method customarily adopted in the fixation of enzymes or in affinity chromatography. As the activation method, there can be mentioned, for example, the cyanogen halide method, the epichlorohydrin method, the bisepoxide method, the triazine halide method, the bromoacetyl bromide method, the ethyl chloroformate method and the 1,1'-carbonyldiimidazole method. The activation method adopted for the production of the adsorbent of the present invention is not limited to the methods exemplified above, but any of the methods using a reagent capable of substitution reaction and/or addition reaction with a nucleophilic group containing an active hydrogen atom, such as an amino, hydroxyl, carboxyl or thiol group, of the low-molecular-weight substance to be fixed can be adopted.

If necessary, a molecule (i.e., spacer) having an optional length may be introduced between the carrier and the low-molecular-weight substance. For example, there may be adopted a method in which the hydroxyl group of the carrier is reacted with one isocyanate group of hexamethylene diisocyanate and the other isocyanate group of hexamethylene diisocyanate is reacted and coupled with the amino, hydroxyl, thiol or carboxyl group of the low-molecular-weight substance. If the length of the spacer is such that the number of atoms included in the spacer is up to 20, especially good results can be obtained.

In the present invention, it is preferred that the low-molecular-weight substance be fixed to the carrier in an amount of 0.1 to 1,000 μmol, preferably 0.5 to 100 μmol, per g of the carrier (in terms of the dry weight).

Fixation of the low-molecular-weight substance to the carrier can be accomplished by utilizing the hydroxyl, amino, carboxyl and phosphoric groups of the low-molecular-weight substance.

The method comprising activating the carrier and fixing the low-molecular-weight substance to the activated carrier has been described in detail as the process for the production of the adsorbent of the present invention, but it must be noted that the process for the preparation of the adsorbent is not limited to the above-mentioned method and that other methods may be adopted. For example, there can be adopted a method in which the low-molecular-weight substance is bonded with a polymerizable monomer or a crosslinking agent and polymerization (or copolymerization) is then carried out and a method in which a crosslinking agent with which the low-molecular-weight substance has been bonded is used at the post-crosslinking step. Furthermore, there may be adopted a method wherein a polymer to which the low-molecular-weight substance can be fixed is coated on the water-insoluble carrier and the low-molecular-weight substance is then fixed thereto, and also a method wherein the low-molecular-weight substance is fixed to a polymer and the water-insoluble carrier is then coated with said polymer. In this case, if necessary, the coated polymer may be post-crosslinked. Moreover, there may be adopted a method in which the low-molecular-weight substance is activated and is then fixed to the carrier.

Figure 2:
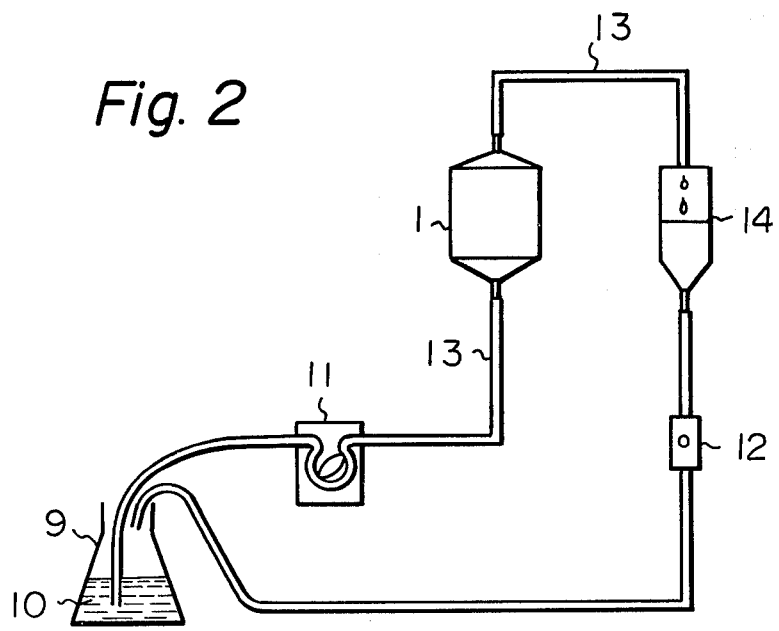
FIG. 2 is a diagram illustrating a model experimental system, used in Examples, including the adsorption apparatus of the present invention.

The adsorption apparatus of the present invention is constructed by packing the above-mentioned adsorbent in a vessel having inlet and outlet openings so that the body fluid passes through the vessel while having contact with the adsorbent. An embodiment of the adsorption apparatus according to the present invention is shown in FIGS. 1 and 2. The adsorption apparatus 1 shown in FIG. 1 comprises caps 6 and 6' fitted through screws 7 and 7', respectively, and packings 4 and 4' having filters 3 and 3' attached to the inner sides thereof are attached to the respective fitted portions. An adsorbent 8 is packed and held in a space formed between the filters 3 and 3'. The above-mentioned adsorbent of the present invention may be singly packed, or said adsorbent may be packed either as a mixture thereof with other adsorbents or in the form of superposed layers, a part of which is comprised of the adsorbent of the present invention and the other of which is comprised of other adsorbents.

When the adsorption apparatus is used for extra-corporeal circulation, it is preferred that the volume of the adsorbent 8 be about 50 to about 400 ml. When the adsorption apparatus of the present invention is used for extra-corporeal circulation, the following two methods are mainly adopted.

According to one method, blood removed from the body is separated into plasma and hemocyte components by a centrifugal separator or a membrane-type plasma separator, the plasma component is passed through the adsorption apparatus of the present invention and is purified, the purified plasma component is combined with the hemocyte components, and the mixture is infused into the body. According to the other method, blood removed from the body is directly passed through the adsorption apparatus of the present invention and is purified.

Since the adsorption efficiency of the immune adsorbent of the present invention is very high, the particle size of the adsorbent can be increased and the pack density of the adsorbent can be reduced. Accordingly, a high passage speed can be assured for either blood or plasma irrespectively of the shape of the adsorbent. Therefore, a large quantity of body fluid can be treated. The body fluid may be circulated continuously or intermittently according to clinical necessity or the installation conditions.

It is considered that the functional mechanism of the adsorbent of the present invention is similar to the mechanism of antigen-antibody reaction. It is quite surprising, however, that in the adsorbent of the present invention, a sufficient adsorption capacity is manifested by the low-molecular-weight substance without using a natural polymer acting inherently as the antigen or a similar synthetic polymer. Furthermore, even if the low-molecular-weight substance used in the present invention is flowed in the living body, it does not cause any trouble but is metabolized in the living body.

The adsorbent and adsorption apparatus of the present invention can specifically adsorb and remove autoantibodies such as the anti-DNA antibodies, anti-ENA antibodies and antinuclear antibodies in the body fluid and/or immune complexes in the body fluid at an enhanced efficiency. Moreover, the apparatus is very compact and adsorption can be performed conveniently and safely. Furthermore, sterilization can be accomplished easily and assuredly. When a crosslinked copolymer comprising vinyl alcohol units as the main recurring units is used as the carrier, non-specific adsorption of plasma proteins is reduced and the mutual reaction between the copolymer and the complement or coagulation system is controlled. Furthermore, the adsorbent has an excellent physical and mechanical strength and is difficult to break or destroy during the manufacturing process or when handled. Moreover, since the adsorbent is rigid, the body fluid can be passed at a high flow rate. In addition, since the adsorbent has an excellent heat resistance, sterilization can be accomplished very easily and assuredly according to a customary method such as the ethylene oxide gas sterilization method, the high-pressure steam sterilization method or the $\gamma$-ray sterilization method. When the adsorbent of the present invention is used as a whole blood adsorbent, since the mutual action between the adsorbent and the hemocyte components is reduced, the occurrence of such undesirable phenomena as thrombosis, non-specific adsorption of the hemocyte components and residual blood is substantially controlled.

The adsorbent of the present invention can be applied to ordinary methods for purification and regeneration of the body fluid, such as the patient's own plasma. The adsorbent of the present invention is used as a remedy for diseases involving autoantibodies such as anti-DNA antibodies, anti-ENA antibodies and antinuclear antibodies and/or immune complexes, for example, SLE, mixed connective tissue disease (MCTD), progressive systemic sclerosis, Sjogren's syndrome, dermatomyositis (multiple myositis), silicosis, rheumatoid arthritis, Hashimoto's disease, chronic hepatitis, diabetes and bronchiectasis. The adsorbent of the present invention is especially effective as a remedy for autoimmune diseases such as systemic lupus erythematodes.

The adsorbent of the present invention is effectively used not only as a remedy for the foregoing diseases while it is packed in the adsorption apparatus but is also effectively used in the separation and purification of autoantibodies such as anti-DNA antibodies and antinuclear antibodies and/or immune complexes and in the examination of these antibodies and immune complexes.

The present invention will now be described in detail with reference to the following Examples that by no means limit the scope of the invention.

EXAMPLE 1

Adenine (supplied by Yamasa Shoyu K. K.) was fixed to CNBr-activated Sepharose 4B (supplied by Pharmacia Co., Sweden, and having an average particle size of 260 $\mu$m) and excessive active groups were blocked by glycine. The adenine retention quantity was calculated from the adsorption at 260 nm, which was observed when the treatment with 6 N hydrochloric acid was carried out at room temperature for 24 hours and the ligand (adenine) was then set free. The so-formed adsorbent was sufficiently washed with physiological saline solution and was used for the test after removal of water.

The adsorption test was carried out by mixing 3 parts by volume of plasma of a patient with 1 part by volume of the adsorbent and performing incubation at 37° C. for 3 hours. For a comparison purpose, the control test was carried out by using unactivated Sepharose 4B.

Formalin-fixed chicken hemocytes sensitized with DNA were mixed with graduated dilutions of treated or untreated plasma of a patient. Whether anti-DNA antibody was positive or negative was determined based on whether or not agglutination reaction took place at room temperature at the time of mixing. The anti-DNA antibody value was expressed by the maximum dilution ratio (times) at which agglutination reaction was positive. DNA test kit (supplied by Fuji Zoki Seiyaku K. K.) was used for the measurement.

A gradually diluted sample (primary antibody) was dropped on a slide glass sheet coated with cells to effect antigen-antibody reaction, and then, peroxidase labeled anti-human immune globulin antibody (secondary antibody) was dropped and the color reaction of the enzyme was observed by an optical microscope. Enzyme ANA test kit (supplied by K. K. Igakuseibutsugaku Kenkyusho) was used for the measurement. The antinuclear antibody value was expressed by the maximum dilution ratio (times) at which the color reaction was positive.

The immune complex quantity was determined according to a method in which immune complexes were precipitated by polyethylene glycol (PEG) and complement hemolytic reaction was carried out. The operation procedures and conditions were as follows.

(1) 0.3 ml of a specimen was poured into a separating tube, and 50 $\mu$l of 0.2 N EDTA was added and the mixture was stirred. Then, 50 $\mu$l of a boric acid buffer solution was further added and the mixture was stirred. Then, 0.1 ml of 12.5% polyethylene glycol (molecular weight=6,000) was added, and the mixture was stirred and allowed to stand at 4° C. for 90 minutes.

(2) The mixture was subjected to centrifugal separation at 4° C. under a load of 1,700 g, and the precipitate was washed with 1.0 ml of 2.5% polyethylene glycol. Centrifugal separation was conducted again under a load of 1,700 g for 15 minutes, and then was supernatant was thrown away.

(3) 30 $\mu$l of GVB++ (gelatin Veronal buffer solution containing divalent cations) maintained at 37° C. was added to the precipitates to dissolve the precipitates therein, and 10 $\mu$l of pooled healthy human serum was added as the complement source. The immune complex was reacted with the complement at 37° C. for 30 minutes.

(4) 1.0 ml of EA (antibody-sensitized erythrocytes) (1.5 $\times$ 10$^8$ per ml) was added to the reaction mixture, and the mixture was shaken at 37° C. for 60 minutes to promote the hemolytic reaction by the residual complement.

(5) After completion of the reaction, 6.5 ml of physiological saline solution maintained at 4° C. was added to the reaction mixture, and centrifugal separation was then conducted and the absorvancy (OD$_{414}$) was measured.

(6) The ratio of inhibition of hemolysis to healthy human serum as the control was calculated according to the following formula. Incidentally, the unit of the inhibition ratio is PEG-CC %.

$$\text{Inhibition Ratio (\%)} = \frac{\text{Absorbancy of Control} - \text{Absorbancy of Specimen}}{\text{Absorbancy of Control}} \times 100$$

$$\text{Removal Ratio (\%)} = \frac{\text{Inhibition Ratio of Untreated Plasma} - \text{Inhibition Ratio of Treated Plasma}}{\text{Inhibition Ratio of Untreated Plasma}} \times 100$$

The sensitized erythrocytes for the measurement of the complement value (KW supplied by Nippon Toketsu-Kanso Kenkyusho) were used as EA.

The albumin quantity was determined according to the albumin measurement method using Bromocresol Green, and A/GB-Test Wakko (supplied by Wakko Junyaku Kogyo K. K.) was used as the reagent. The ratio of the amount of albumin reduced after the adsorption test to the amount of albumin in patient's plasma was determined as the removal ratio.

The obtained results are shown in Table 1.

EXAMPLE 2

The procedures of Example 1 were repeated in the same manner except that 5-aminouracil was used as the ligand (low-molecular weight substance) to be fixed. The obtained results are shown in Table 1.

EXAMPLE 3

The procedures of Example 1 were repeated in the same manner except that guanine was used as the ligand to be fixed. The obtained results are shown in Table 1.

EXAMPLE 4

The procedures of Example 1 were repeated in the same manner except that guanosine was used as the ligand to be fixed. The obtained results are shown in Table 1.

EXAMPLE 5

The procedures of Example 1 were repeated in the same manner except that cytidine 5'-phosphate (CMP) was used as the ligand to be fixed. The obtained results are shown in Table 1.

EXAMPLE 6

The procedures of Example 1 were repeated in the same manner except that adenosine 5'-phosphate (ADP) was used as the ligand to be a fixed. The obtained results are shown in Table 1.

EXAMPLE 7

The procedures of Example 1 were repeated in the same manner except that nicotinamide-adenine dinucleotide (NAD) was used as the ligand to be fixed. The obtained results are shown in Table 1.

EXAMPLE 8

0.5-denier Bemberg filaments (supplied by Asahi Kasei Kogyo K. K.) were activated with CNBr according to customary procedures, and adenine was fixed to the so-prepared carrier. Then, 1 g of the so-obtained adsorbent and 10 ml of plasma of a patient were subjected to incubation at 37° C. for 3 hours. Untreated Bemberg filaments were used as the control. Other procedures and conditions were the same as described in Example 1. The obtained results are shown in Table 1.

EXAMPLE 9

A terpolymer derived from hydroxyethyl methacrylate, ethylene glycol dimethacrylate and glycidyl methacrylate and having an average particle size of 500 μm an average pore size of 1,500 Å and an epoxy density of 1 mol %, which was activated with CNBr, was used as the vinyl type porous polymer carrier. Adenine was fixed to this terpolymer. The unreacted expoxides wire blocked with glycine.

The adsorption test was carried out in an experiment system illustrated in FIG. 2 by using 10 ml of the so-prepared adsorbent.

A vessel 9 was charged with 30 ml of plasma 10 of a patient and plasma was pumped out at a rate of 1 ml/min by a pump 11. A tube 13 was set so that plasma was returned to the vessel 9 through a drip chamber 14 and a sampling opening 12.

Blood of the same patient was circulated for 3 hours by the above-mentioned apparatus, and blood was sampled, and the quantities of autoantibodies and immune complexes in the plasma were measured in the same manner as described in Example 1. An untreated vinyl type porous polymer carrier was used as the control. The obtained results are shown in Table 1.

TABLE 1

| Example No. | Fixed Material | Carrier | Retention Quantity (mol/g) | Anti-DNA Antibody Value | Anti-Nuclear Antibody Value | Immune Complex Removal Ratio (%) | Albumin Quantity (g/dl) |
|---|---|---|---|---|---|---|---|
| 1 | Patient's plasma | | — | 320 | 1280 | — | 2.7 |
| | Adenine | Sepharose 4B | 48 | 10 | 40 | 86 | 2.4 |
| | — | Sepharose 4B | — | 320 | 1280 | 4 | 2.6 |
| 2 | 5-Aminouracil | Sepharose 4B | 15 | 40 | 160 | 75 | 2.5 |
| 3 | Guanine | Sepharose 4B | 20 | 20 | 80 | 84 | 2.4 |
| 4 | Guanosine | Sepharose 4B | 18 | 40 | 160 | 80 | 2.5 |
| 5 | CMP | Sepharose 4B | 7 | 80 | 160 | 75 | 2.5 |
| 6 | ADP | Sepharose 4B | 9 | 80 | 160 | 76 | 2.5 |
| 7 | NAD | Sepharose 4B | 9 | 160 | 320 | 62 | 2.4 |
| 8 | Adenine | Bemberg | 32 | 20 | 40 | 80 | 2.4 |
| | — | Bemberg | — | 320 | 1280 | 6 | 2.3 |
| 9 | Adenine | Vinyl type porous terpolymer | 40 | 10 | 80 | 90 | 2.4 |
| | — | Vinyl type porous terpolymer | — | 320 | 1280 | 7 | 2.3 |

EXAMPLE 10

A flask was charged with a homogeneous liquid mixture of 100 g of vinyl acetate, 24.1 g of triallyl isocyanurate (X=0.20), 124 g of ethyl acetate, 124 g of heptane, 3.1 g of polyvinyl acetate (polymerization degree=500) and 3.1 g of 2,2'-azobisisobutyronitrile and 400 ml of an aqueous solution containing 1% by weight of polyvinyl alcohol, 0.05% by weight of sodium dihydrogenphosphate dihydrate and 1.5% by weight of disodium hydrogenphosphate dodecahydrate. The mixture was sufficiently stirred and heated at 65° C. for 18 hours and at 75° C. for 5 hours to effect suspension polymerization whereby a granular copolymer was obtained. The obtained copolymer was recovered by filtration, washed with water and extracted with acetone. Thereafter, hydrolysis reaction of the copolymer was carried out at 40° C. for 48 hours in a solution comprising 46.5 g of sodium hydroxide and 2 l of methanol. The average particle size of the obtained particles was 150 μm. When the hydroxyl group density (qOH) was determined according to the above-mentioned method, it was found that the hydroxyl group density was 13 meq/g.

The obtained gel was packed in a stainless steel column having an inner diameter of 7.5 mm and a length of 25 cm. An aqueous solution of various dextrans and polyethylene glycols differing in the molecular weight and a phosphoric acid buffer solution of albumin, immunoglobulin G, immunoglobulin M and β-lipoprotein were passed through the packed column. In each case, the solutes were dissolved out in the order of the molecular weight. The rejection critical molecular weight of the dextrans was about $3 \times 10^5$ and the rejection critical molecular weight of the proteins was about $18 \times 10^5$. When an aqueous solution containing 0.3 M of sodium chloride and 0.1 M of sodium phosphate was used as a solvent and a solution containing each of human-γ-globulin and human-alubumin in said solvent was passed through the packed column, the globulin and albumin were recovered substantially completely and non-specific adsorption was substantially controlled. Incidentally, each test was carried out at a flow rate of 1 ml/min.

Then, 50 cc of the hydrolyzed gel washed sufficiently with water was suspended in 200 ml of water and 3 g of cyanogen bromide was added to the suspension, and the mixture was stirred. Reaction was carried out for 8 minutes while maintaining the pH value at 10 to 11 by adding a 2 N aqueous solution of sodium hydroxide and maintaining the temperature up to 10° C. After completion of the reaction, the reaction mixture was filtered by using a glass filter and washed with 2 l of water to obtain an activated gel. Adenine (supplied by Yamasa Shoyu K. K.) was fixed to the activated gel according to customary procedures and the excessive active groups were blocked with glycine. The gel was treated for 24 hours at room temperature with 6 N hydrochloric acid to set the ligand free and the retention quantity was calculated from the absorption at 260 nm. It was found that the retention quantity was 105 μmol/g. The so-prepared adsorbent was sufficiently washed with physiological saline solution and dehydrated, and then, the adsorbent was used for the test.

At the adsorption test, 1 part by volume of the adsorbent was mixed with 3 parts by volume of plasma of a patient suffering from the systemic lupus erythematodes, and incubation was carried out at 37° C. for 3 hours. Unactivated hydrolyzed gel was used as the control. The obtained results are shown in Table 2.

From the results shown in Table 2, it will readily be understood that adenine fixed to a crosslinked copolymer comprising vinyl alcohol units as the main recurring units specifically adsorbs anti-DNA antibodies, antinuclear antibodies and immune complexes at high efficiencies.

TABLE 2

| Specimen | Anti-DNA Antibody Value | Anti-nuclear Antibody Value | Immune Complex Removal Ratio (%) | Albumin Quantity (g/dl) |
|---|---|---|---|---|
| Starting plasma | 320 | 640 | — | 2.8 |
| Plasma after adsorption | 10 | 20 | 89 | 2.6 |

EXAMPLE 11

A vessel similar to that illustrated in FIG. 1 was packed with 5 ml of the immune adsorbent obtained in Example 10. In this manner, two adsorption apparatuses were constructed. The adsorption test was carried out in the experimental system illustrated in FIG. 2 by using these adsorption apparatuses. Incidentally, one adsorption apparatus was sterilized by high pressure steam and used for the test, whereas the other apparatus was not sterilized.

Referring to FIG. 2, the vessel 9 was charged with 20 ml of plasma 10 of a patient suffering from the systemic lupus erythematodes, and the plasma was pumped out at a flow rate of 0.5 ml/min by the pump 11 and fed to the adsorption apparatus 1. The tube 13 was set so that the plasma was returned to the vessel 9 through the drip chamber 14 and the sampling opening 12.

In the above-mentioned adsorption apparatus, the plasma was circulated for 1 hour, and the plasma was sampled and the protein quantities were determined. The obtained results are shown in Table 3.

TABLE 3

| Specimen | Anti-DNA Antibody Value | Anti-nuclear Antibody Value | Immune Complex Removal Ratio (%) | Albumin Quantity (g/dl) |
|---|---|---|---|---|
| Starting plasma | 80 | 640 | — | 2.9 |
| Plasma after adsorption | | | | |
| Not sterilized | 20 | 40 | 76 | 2.7 |
| Sterilized | 20 | 40 | 73 | 2.7 |

We claim:

1. An adsorbing material for autoantibodies and immune complexes comprising a water-insoluble carrier, which is a hydroxyl group-containing crosslinked copolymer having a specific surface area of at least 5 m²/g, and at least one member selected from low-molecular-weight substances containing a purine base or pyrimidine base as a constituent element, which is fixed to said carrier.

2. An adsorbing material as set forth in claim 1, wherein the low-molecular-weight substance is at least one member selected from adenine, guanine, cytosine and uracil.

3. An adsorbing material as set forth in claim 1, wherein the low-molecular-weight substance is ribonucleoside or deoxyribonucleoside.

4. An adsorbing material as set forth in claim 1, wherein the hydroxyl group-containing crosslinked copolymer is a crosslinked copolymer comprising vinyl alcohol units as the main constituent.

5. An adsorbing material as set forth in claim 4, wherein the crosslinked copolymer comprising vinyl alcohol units as the main constituent is a crosslinked polyvinyl alcohol obtained by hydrolyzing a copolymer of a vinyl ester of a carboxylic acid with a vinyl compound having an isocyanurate ring.

6. An adsorbing material as set forth in claim 1, wherein the hydroxyl group-containing crosslinked copolymer has a hydroxyl group density of 5 to 17 meq/g.

7. An adsorbing material as set forth in claim 1, wherein the hydroxyl group-containing crosslinked copolymer has a molecular weight exclusion limit for protein of from 150,000 to about 10,000,000.

8. An apparatus for adsorption of autoantibodies and immune complexes, which comprises a vessel having fluid inlet openings and fluid outlet openings and at least one adsorbing material packed in said vessel, said adsorbing material comprising a water-insoluble carrier, which is a hydroxyl group-containing crosslinked copolymer having a specific surface area of at least 5 $m^2/g$, and at least one member selected from low-molecular-weight substances containing a purine base or pyrimidine base as a constituent element, which is fixed to said carrier.

9. A method for removing at least one of an autoantibody and an immune complex from body fluid, comprising contacting body fluid containing at least one of an autoantibody and an immune complex with an adsorbing material comprising a water-insoluble carrier, which is a hydroxyl group-containing crosslinked copolymer having a specific surface area of at least 5 $m^2/g$, and at least one member selected from low-molecular weight substances containing a purine base or pyrimidine base as a constituent element, which is fixed to said carrier.

* * * * *